United States Patent [19]
Skala

[11] 3,936,192
[45] Feb. 3, 1976

[54] OPTICAL FLUID CONTAMINATION AND CHANGE MONITOR

[75] Inventor: George F. Skala, Scotia, N.Y.

[73] Assignee: Environment/One Corporation, Schenectady, N.Y.

[22] Filed: Apr. 19, 1973

[21] Appl. No.: 352,614

Related U.S. Application Data

[63] Continuation of Ser. No. 847,675, Aug. 5, 1969.

[52] U.S. Cl. .............................. 356/104; 356/201
[51] Int. Cl. ............................................ G01n 21/00
[58] Field of Search .......... 356/103, 104, 180, 181, 356/201, 204, 206, 244, 246; 324/130, 140 R

[56] References Cited
UNITED STATES PATENTS

| | | | |
|---|---|---|---|
| 2,873,644 | 2/1959 | Kremen et al. | 356/104 |
| 2,877,453 | 3/1959 | Mendenhall, Jr. | 356/103 |
| 3,470,381 | 9/1969 | Boyd | 356/201 |

*Primary Examiner*—Ronald L. Wibert
*Assistant Examiner*—Conrad Clark
*Attorney, Agent, or Firm*—Charles W. Helzer

[57] ABSTRACT

An optical oil monitor that measures particle contamination in oil by passing light through an oil sample and picking up the light that is scattered at 90° by the particle contaminaton and measures chemical breakdown by the attenuation of the light passing substantially straight through the oil with a second sensor. Alternately a sample and a reference are passed between the light responsive sensors for error correction and calibration so that each sensor will have an output signal alternating between a sample signal and a reference signal. A control signal of the same frequency is provided in combination with a plurality of gates to separate the sample and reference signals. The attenuation reference signal is compared to a standard signal to produce an error output for regulating the intensity of the light source to compensate for power source fluctuations, lamp characteristic changes, window soiling and the like. The scattering reference signal is used to adjust the gain on the scattering sample signal amplifier to obtain the desired output from the sample circuit peak detector. The sample and reference are housed within a rotor provided with vanes so that it may be driven as a pump by a motor or be driven by fluid flow as a turbine. When the rotor acts as a turbine, the frequency of the light responsive sensors will be correlated to the fluid flow so that an appropriate frequency responsive gauge is provided in circuit to monitor the fluid flow. Also, a malfunction light will signal the absence of a reference attenuation signal.

28 Claims, 9 Drawing Figures

FIG. 9

OPTICAL FLUID CONTAMINATION AND CHANGE MONITOR

This is a continuation of application Ser. No. 847,675, filed Aug. 5, 1969.

BACKGROUND OF THE INVENTION

In lubrication systems for internal combustion engines and hydraulic systems for the control of mechanisms, it is important to know the condition of the oil that is circulated in that excess particle contamination will not only increase the wear rate of moving parts, but that it will also indicate the impending failure of a moving part, for example a bearing, and the chemical breakdown or other change in the oil will mean that its flow characteristics have changed and that it will in many times no longer be suited for its intended purpose. Also, in fuel lines, particularly for aircraft engines, it is important to know if particle contamination is present which would block small conduits, particularly during carburation and if there is a chemical change in the fuel so that it would not properly burn. Also, there are many other areas where it is important to know the particle content of a fluid and its chemical composition, for example for oil well drilling or in water purification.

Optical systems having been used in the past, because of their accuracy and convenience in monitoring some of the above characteristics for fluids. Particularly, particle contamination will produce a scattering of light passed through a fluid and chemical breakdown or other change will affect the transmissibility of the fluid for light passing substantially straight through it. However, such systems are susceptible to considerable errors during long term operation in that light source intensity may change due to voltage fluctuations or changes in the light producing element itself; also, window discoloration and other contamination will have similar effects on the light that is eventually picked up by the light responsive sensors. These error causing factors will produce false readings for the desired characteristics. There has been no satisfactory way in which to compensate for these errors.

Although reference signals are known, such signals applied to the above systems would not provide true references, because they employ different light source elements and different pickups from those of the sample system so that a light source variation in the sample system would not necessarily be picked up in the reference system. Thus, such an arrangement would only be a partial solution.

Fluid monitoring systems in the past have been quite bulky, and involving many components that will correspondingly increase the likelihood of failure. Also complete failure indicators are not generally provided.

SUMMARY OF THE INVENTION

It is an object of the present invention to overcome the abovementioned disadvantages by providing an oil monitoring system that has a feedback regulating circuit lamp intensity that is independent of or corrects the various errors mentioned above. The oil monitor of the present invention is compact and simple for corresponding economies. Also, it is versatile in that it will monitor two or more characteristics of the fluid, correct for errors, show malfunction, and indicate flow rate.

The oil monitor is an on-board real time indicator of the optical properties of the lubrication oil for a gas turbine powered aircraft. Any lubrication system with a circulating oil supply can also be monitored by this device. The instrument is composed of a detector cell through which the lubricating oil passes, and an appropriate electronic data processing circuitry. The latter component may be located in the engine housing or at a remote location.

The function of the oil monitor is to measure the attenuation of a beam of light traversing a given path length of oil, and the amount of light scattered from a volume of the oil. The light attenuation is a measure of chemical degradation of the oil, while the scattering is a function of particulate contamination. For successful long term stable operation, these measurements must be free of effects due to light source variations, window discoloration, and changes in light sensor characteristics. Also, the monitor must not impair the integrity of the oil system, which requires a design to minimize the possibility of catastrophic failure due to leakage or plugging of the monitor head.

The present invention employs a reference attenuation and scattering medium for periodically displacing the oil in order to provide stable reference levels. This is accomplished by a rotor rotating within the flow of oil. The rotor may be divided into two or four segments, with half of the segments containing semi-transparent material which will have a scattering property and an attenuation property similar to that of clean oil or other fluid employed. The other half of the segments will contain short windows with most of the light passed containing fluid to be monitored. Also, it is contemplated that color filters may be used so that from the same light source, light having one predominate color will be passed through one set sample and reference material while light of a different color will be passed through another set of sample and reference material. The short windows will introduce the same amount of attenuation into the ends of the sample paths as is normally produced for the ends of the reference paths.

A single light source is provided for all of the sample and reference materials and is conducted thereto and therefrom by means of fiber optics. Reflecting portions on the rotor produce a signal on a light responsive sensor to indicate to the circuitry when the reference is being measured or alternatively when the sample is being measured.

With the present invention, the system is independant of the direction of rotation, so that it may be employed with fluid flowing in either direction through the monitor so that the fluid will impinge upon the rotor reaction vanes to provide a turbine action for rotating the rotor, which will in turn produce signals from the light responsive sensors that will have a frequency correlated to the fluid flow, which fluid flow may be indicated by suitable known frequency responsive flow gauge or the like. Also, the rotor may be driven by a suitable motor means so that its peripheral vanes act as a pump for circulating the sample fluid. The system may be easily designed to operate over a wide range of signal frequencies, so that the oil flow rate may vary over a wide range. For example, the unit may operate in flow rate ranges between 1.5 and 20 gallons per minute. The absence of a reference identification signal or a control signal may be used to trigger a malfunction light or other indicator to show a system breakdown such as light source failure or stoppage of the rotor.

The present invention provides a low flow resistance path through the optical system when operating as a turbine.

The present invention provides circuitry for frequent and automatic adjustment of the optics to maintain constant response to a reference signal. Suitable feedback in regulating circuitry is provided to be operated by the reference signals to eliminate the effects of light source variation, window and fiber optics transmission changes, photo cell or other sensor variations, etc. Also, the reference scattering signal is used as a calibration standard for the scattering light measurement, thus removing the effects of variation of the scattering light sensor. Photo-resistive cells may be used in that they are available over a wide range of characteristics, ratings, etc. Their sensitivity, linearity and stability have been established through other uses, for example where they have been able to measure as few as one hundred droplets per cubic centimeter of air, which droplets measure about five microns in diameter. This represents a sensitivity on the order of one part in one hundred million, based on volume ratios. By using similar circuit techniques, the detection of ten parts per million of oil impurities can be readily accomplished. Also, phototransistors may be used instead of photo-resistive cells.

The versatility of the present invention is shown by the fact that units may be easily constructed for operation with 115 Volt, 60 cycle power or 28 Volt D.C. power or 400 cycle, 115 Volt power, for example. Total power used to operate the oil monitor is about ten watts and its weight when capable of handling a flow of 20 gallons per minute is about 2 pounds. The instrument output is preferably 0–5 Volts D.C. on two channels, one for attenuation and the other for scattering.

With the use of common light responsive sensors for each of the reference sample light pickups, output signals will be produced having a frequency corresponding to the alternation between the sample and reference. A further light responsive sensor combined with at least one reflective surface on the rotor produces a control signal of the same frequency, which may be phase inverted to produce two control frequencies respectively in phase with the sample and reference signals to operate gates in the test and reference circuits for passing only the corresponding test and reference signals. Furthermore, the alternating outputs of the sensors have the advantage that D.C. eliminators may be used in the circuits for removing D.C. current that would be produced by stray light, circuit noise, etc, which would produce false readings.

BRIEF DESCRIPTION OF THE DRAWING

Further objects, features and advantages of the present invention will become more clear from the following detailed description of preferred embodiments of the present invention shown in the attached drawing wherein:

FIG. 5 is a partial cross sectional view taken along line V—V of FIG. 3 to show the window, oil outlet, and scattered light outlet for the sample holding passage;

DETAILED DESCRIPTION OF THE DRAWING

Figure 1:
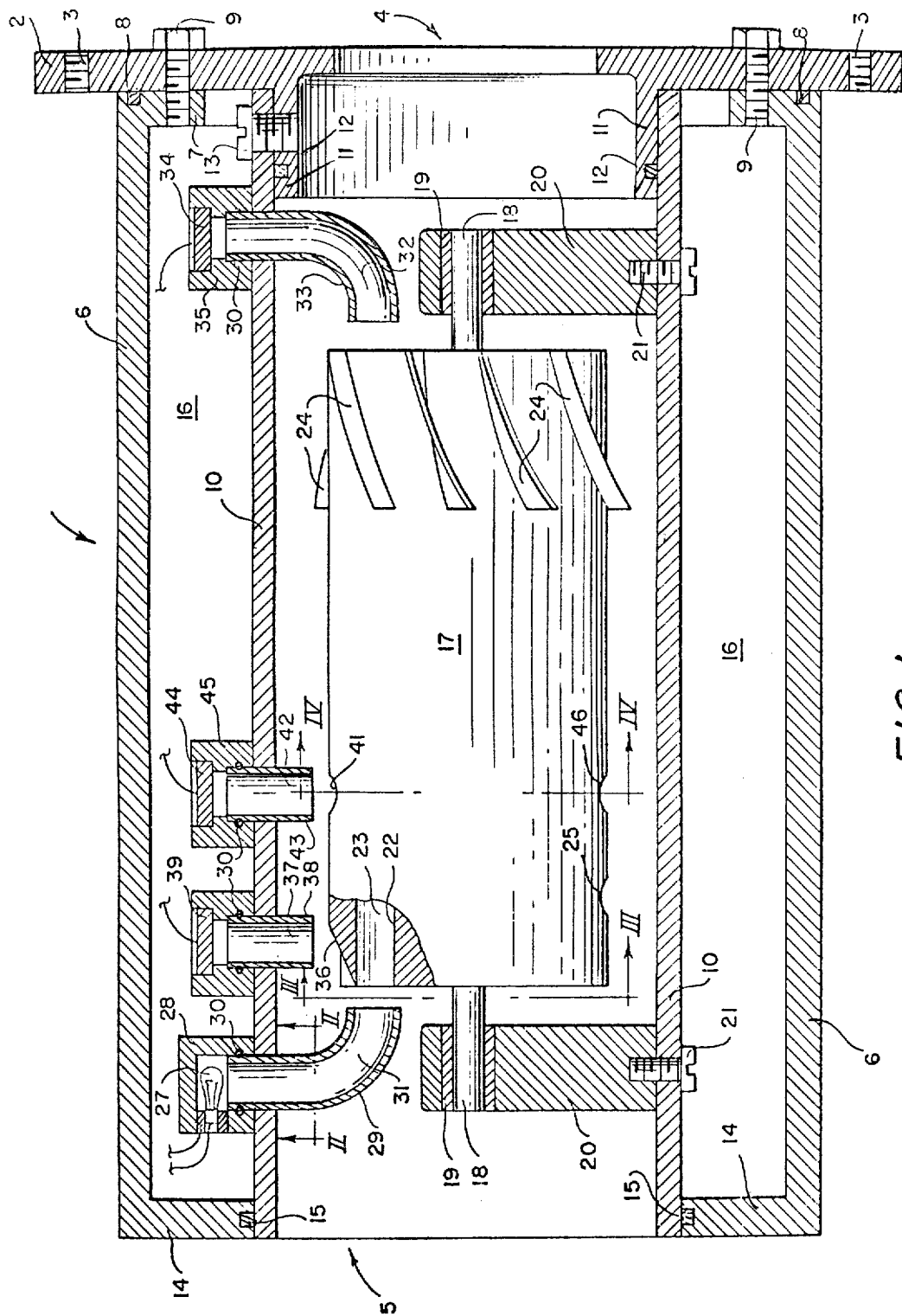
FIG. 1 is a longitudinal cross sectional view through the mechanical portion of the oil monitor that is inserted in a fluid sample passing light through the sample and producing electrical signals in proportion to the effect the sample and a reference have upon the light.

As shown in FIG. 1, the generally cylindrical mechanical portion of the oil monitor according to the present invention comprises a body portion 1 that is mounted within an area containing the sample material to be monitored, for example, which is mounted below the oil level in an internal combustion engine lubricating oil sump. To facilitate this mounting, the body portion 1 is provided with an annular flange 2 which has a plurality of peripheral threaded or through bores 3 to receive mounting screws (not shown). The body portion 1 provides a central through passageway for the sample material, which will hereafter be referred to as lubricating oil for purposes of a specific example. The oil may enter or exit from respectively either the central aperture 4 in the annular flange 2 or the aperture 5 at the other end of the body portion 1.

To form the central passageway, the body portion 1 is provided with an outer tube 6 that has an entrance flange 7 (the aperture 4 being considered the entrance for purposes of a specific example). The flange 7 is provided with an annular recess containing therein an O-ring 8 for providing a fluid tight seal with the annular flange 2 when the outer tube 6 and annular flange 2 are rigidly secured together by means of the peripherally arranged screws 9.

An inner tube 10 is concentrically mounted within the outer tube 6 by means of a telescoping engagement with an integral tubular portion 11 of the annular flange 2. The tubular portion 11 has a peripheral outer recess containing therein an O-ring 12 providing sealing engagement with the inner tube 10, and the screw 13 secures the assembly against relative axial movement. The exit end of the inner tube 10 is concentrically engaged with an inturned annular flange 14 of the outer tube 6; the inner periphery of the annular flange 14 is provided with an annular recess containing therein an O-ring 15. Thus, there is formed an annular fluid tight air chamber 16 between the outer tube 6 and the inner tube 10, with the central through passageway being a part of the usual sealed lubricating oil sump of an internal combustion engine. The air chamber 16 will house the electrical components of the unit while the central through passageway will have therein the mechanism for containing and moving the sample material and reference material.

Figure 3:
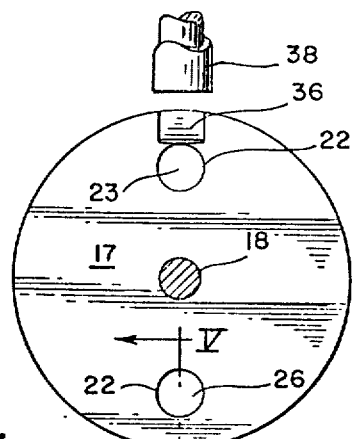
FIG. 3 is a cross sectional view showing the reference and sample passages in the rotor along with the control reflecting surface on the rotor and the associated stationary control optical fiber, as viewed from line III—III in FIG. 1.
Figure 4:
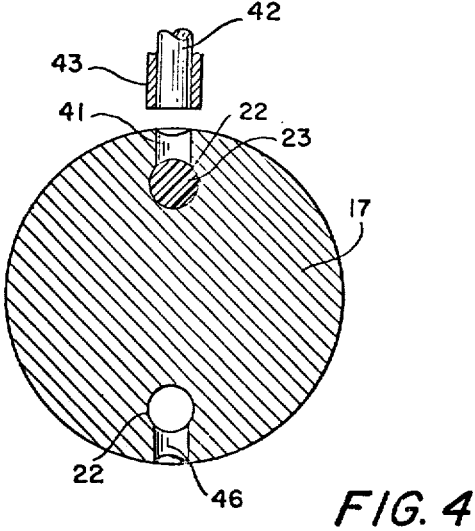
FIG. 4 is a cross sectional view of the rotor showing the light scattering passages and the stationary optical fiber for picking up the scattered light, which is taken along line IV—IV of FIG. 1.

Concentrically within the central passage way is a rotor 17 rotatably mounted by means of opposed stub shafts 18 that are respectively received within the two sleeve bearings 19 that are carried by means of pillow blocks 20. The pillow blocks 20 are rigidly secured to the inner surface of the inner tube 10 by means of suitable screws 21, welding or the like. As shown more particularly in FIGS. 3 and 4, the rotor 17 has two diametrically opposed axially extending through passages 22, one of which has therein the reference material, for example, a Pyrex glass rod 23. The rod 23 may be constructed of any light conducting or passing material that will approximate the desired optical characteristics or properties of the sample to be tested, with the sample in an acceptable condition. The other through passage 22 contains therein the sample material, such as oil, to be tested and monitored. Around the entrance periphery of the rotor 17 there are provided a plurality of radially extending blades or vanes 24 that will act as turbine blades to rotate the rotor 17 when oil moves through the central through passageway in either direction or alternatively, a suitable motor may be connected to one of the stub shafts 18 to drive the rotor 17 so that the blades 24 will act as axial pump blades for moving the oil through the central passageway. In either event, the oil will continuously move through the sample passage 22 by entering at the entrance end, traveling axially and exiting from the slanted outlet 25 shown in FIG. 5. With the rotor 17 rotating, centrifugal force will tend to move the oil radially outwardly through the outlet passage 25 to provide a pumping action for moving the oil axially through the passage 22 from the entrance towards the exit. As shown in FIG. 5, the exit end of the sample passage 22 is provided with a glass or plastic disc window 26 which will have two faces exposed to the oil for approximating the discoloration or clouding effect produced on the opposed ends of the reference material rod 23.

As further shown in FIG. 1, a suitable light source 27 is mounted within housing 28 secured by welding or the like to the outer surface of the inner tube 10. A protective tube 29 extends from within the housing 28 aligned with the light source 27 through the unit tube 10 to where it is bent 90° so that its end has its axis parallel to the adjacent through passage 22. A suitable O-ring or bead and recess snap coupling 30 is provided to securely hold the protective tube 29 within the housing 28 and form a fluid tight seal. The snap coupling is particularly desirable if the elements are made from resiliant plastic material. Within the protective tube 29, there is disposed for its full length an optical fiber 31 which has substantially the same outer diameter as the inner diameter of the protective tube 29 with the intervening space being filled with a suitable sealing material and conducts the light from the light source 27 to within the central through passageway so that it is projected axially through the adjacent passage 22 of the rotor 17. After traversing the aligned through passage 22, the light is picked up by means of an optical fiber 32 contained within a protective tube 33 where it is conducted to impinge upon the sensitive surface of a photo-transistor 34, which is suitably mounted within housing 35 that is welded to the outer surface of the inner tube 10. The light picked up by the optical fiber 32 will be affected by the attenuation characteristics of the material within the aligned through passage 22, for example the chemical breakdown of the lubricating oil. This attenuation will have a corresponding effect upon the output signal produced by the photo-transistor 34.

Immediately adjacent the through passage 22 having therein the reference material 23, there is a reflective surface 36 on the outer periphery of the rotor 17 so that light being projected by the optical fiber 31 is reflected radially to be picked up by the radially aligned optical fiber 37 sealed within the protective tube 38, so that the reflected light is directed to the sensitive surface of a control photo-transistor 39. Thus, the photo-transistor 39 will have an output control signal indicative of the position of the rotor 17, that is a signal pulse will be produced by the photo-transistor 39 each time that the reference material 23 is aligned between the optical fibers 31 and 32. It is also contemplated that the reflective surface 36 could be adjacent the through passage 22 carrying the lubricating oil, instead of in its indicated position, in which case a control signal pulse would be produced each time that the sample material is aligned between the optical fibers 31, 32. The photo-transistor 39 is contained within a suitable housing 40, which is similar to the previously mentioned housings 28, 35, and has correspondingly similar O-ring or coupling 30.

Particle contamination within the oil sample and the optical properties of the reference material 23 will scatter the light traveling therethrough. The light scattered by the reference material 23 will move at right angles to the axis of its passage 22 where some of it will escape through the additional radial passage 41 where it will be picked up by the aligned optical fiber 42 carried within the protective tube 43 so that it will impinge upon the lower sensitive surface of the photo-transistor 44 that is carried in the housing 45. The housing 45 is constructed and mounted similarly to the previously described housings. The photo-transistor 44 will produce an output electrical signal correlated to the scattering effect of the reference material 23. In a like manner, the light scattered by the oil sample, when the oil sample passage 22 is aligned between the optical fibers 31, 32, will pass through the radially extending additional passage 46 to be picked up by the optical fiber 42 to produce a corresponding electrical scattering signal with a photo-transistor 44.

It is also contemplated that four passages 22 may be symetrically spaced about the axis of rotation of the rotor 17 so that there will be two pairs of diametrically opposed reference and sample holding passages 22 and correspondingly twice as many reflecting surfaces 36, outlets 25, additional passages 41, 46, etc. within the rotor. Thus, the signals produced by the photo-transistors 39, 44 and 34 would have twice the frequency of the previously described system. Other combinations are contemplated.

Figure 6:
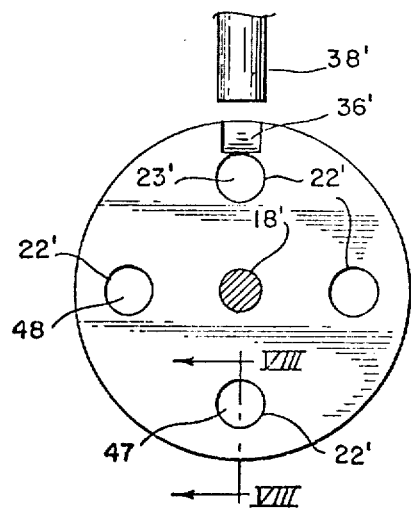
FIG. 6 is a cross sectional view, which is similar to the view of FIG. 3, but which is of a modification wherein four sample and reference passages are shown in the rotor to increase the frequency of the signal output or determine color detecting characteristics of the sample material.
Figure 7:
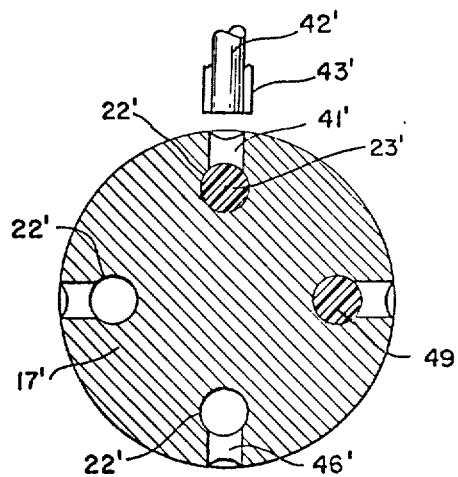
FIG. 7 is a cross sectional view, which is similar to the view of FIG. 4, but of the modification of FIG. 6.
Figure 6:
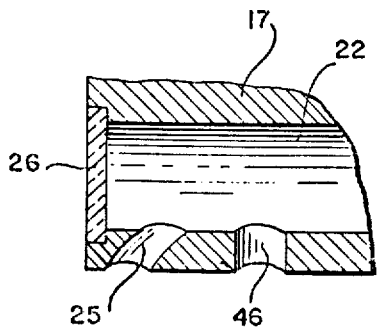
Figure 8:
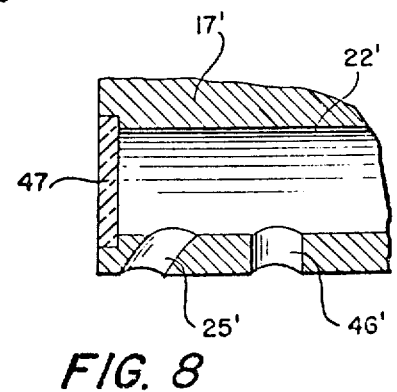
FIG. 8 is a partial cross sectional view taken along line VIII—VIII of FIG. 6 showing the color filter window in place.

A modification of the previously perferred embodiment is shown in FIGS. 6, 7, 8, wherein like numerals are used to describe like previously described elements. In FIG. 8, the window 47 has the same function as the window 26 previously described but in addition is a filter for primarily decreasing a particular color frequency in the light passing therethrough so the light passing through the oil held within the passage 22' will be colored. As seen in FIGS. 6 and 7, another set of diametrically opposed passages 22' are provided in the rotor 17', one of which has therein a filter window 48 identical to the filter window 47, except that it will decrease a different color component of the light. Thus, the oil sample may be monitored with two different colors of light coming from the same light source for determining still further the characteristics of the oil. The reference material 23' would be provided with a light affecting characteristic by suitable filters or the like that would correspond to clean oil in combination with the filter 47. Similarly, a reference material 49 is provided to have the optical characteristics corresponding to the filter window 48 in combination with clear oil. Except for the above described differences, the modification according to FIGS. 6–8 would also employ structure identical to that shown in FIG. 1, so that further description is unnecessary.

Figure 9:
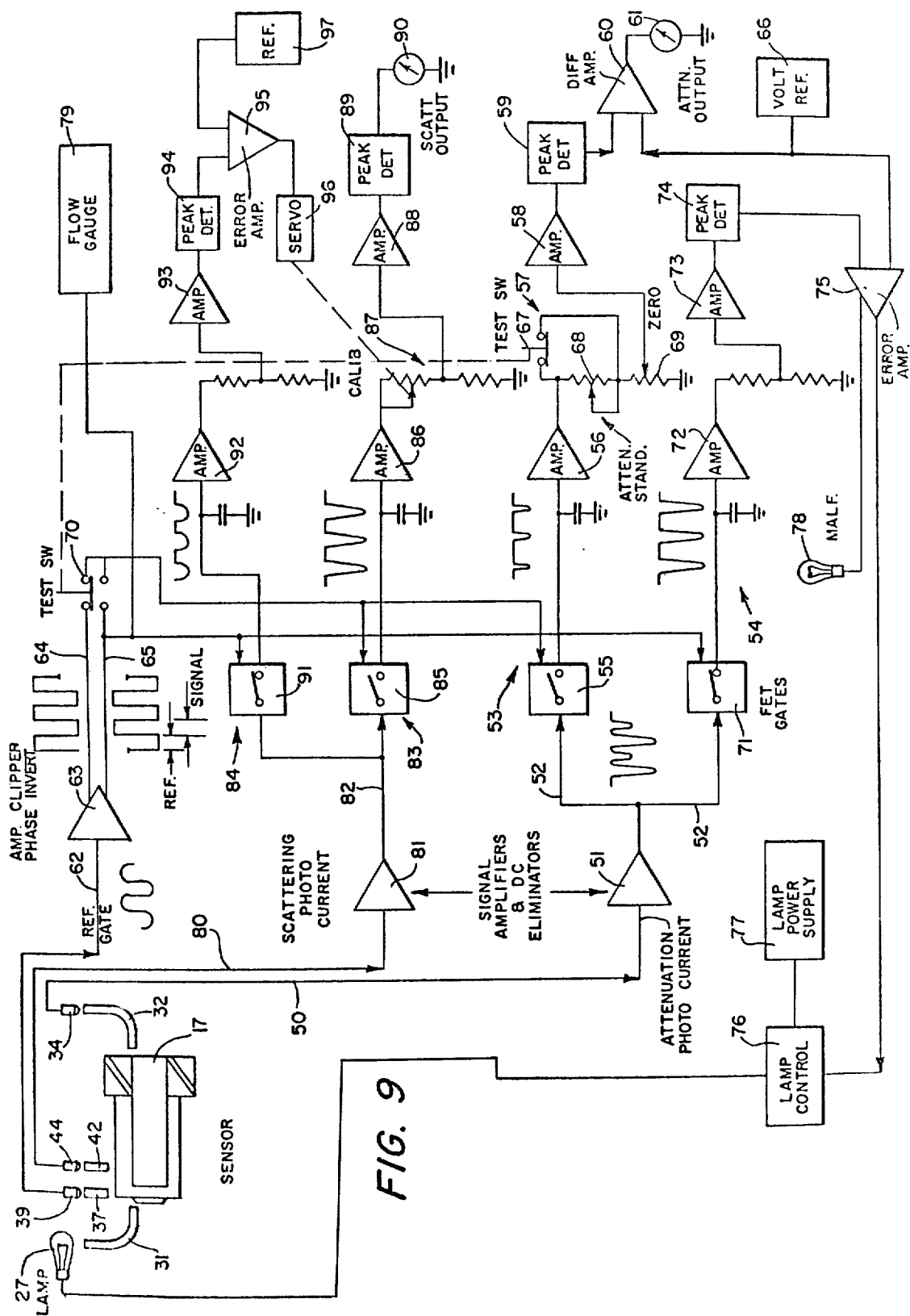
FIG. 9 is a diagram of the electric circuit employed with the oil monitor of the present invention in combination with a schematic representation of the mechanical portion of FIG. 1.

In FIG. 9, there is shown the electrical circuitry to be used in combination with the structure previously described with respect to FIGS. 1–5. With rotor 17 rotating during operation of the sensor shown in FIG. 1, the signal output of the attenuation photo-transistor 34 will be composed of alternating pulses corresponding to the light attenuation characteristics of the reference material and the sample material; this attenuation signal will be conducted by line 50 to the input of signal amplifier and D.C. eliminator 51, where any direct current component of the signal will be blocked or eliminated and the alternating current attenuation signal will be amplified. It is an important feature of the present invention to eliminate the direct current component, which might be caused by stray light affecting the photo-transistor 34 or background disturbances in the circuitry, which would cause errors in the monitoring unless eliminated. The output of the amplifier and D.C. eliminator 51 is split and fed by lines 52 to the parallel attenuation test or sample circuit 53 and attenuation reference circuit 54. The attenuation sample circuit 53 has connected in series circuit a field effect normally open gate 55 for passing only the sample signal pulses, an amplifier 56, a calibration component 57, an amplifier 58, a peak detector 59, a differential amplifier 60, and an attenuation output (preferably a gauge) 61. The control signal produced by the photo-transistor 39 will have a pulse occurring each time that the reference material is aligned with the optical fibers 31, 32. This pulse will be transmitted by line 62 to an amplifier, clipper and phase inverter 63, which has two outputs 64 and 65. The control output signal in line 64 will have a square wave pulse each time that the sample material is aligned with the optical fibers 31, 32, and this control output signal is fed to the field effect transistor gate 55 to close the gate each time a sample attenuation signal appears in input line 52. Thus, only the sample attenuation signal will be amplified by amplifier 56. The differential amplifier 60 receives a standard reference voltage from the reference voltage component 66, compares this with the attenuation sample signal received from the peak detector 59 and produces a differential output that is fed to and operates the gauge 61. The calibration component 57 is further used to adjust the zero reading on the gauge 61 when test switch 70 is depressed to feed the control output signal from output 65 to the gate 55 so that the reference signal only is passed through the attenuation sample circuit 53. Thus, when the signal amplitude is a maximum, corresponding to zero attenuation, the output of the differential amplifier is zero. Operation of test switch 70 simultaneously opens switch 67, so that the attenuation reference signal will pass through the resistance of rheostat 68 which can be set to make zero attenuation correspond to the attenuation of the clean oil.

The attenuation reference circuit 54 has in series circuit a field effect transistor gate 71 that is shown closed because in all of the previous figures the reference material has been shown as aligned between the optical fibers 31 and 32, an amplifier 72, an amplifier 73, a peak detector 74, a differential amplifier 75, a lamp control component 76, and light source 27. The control signal output in line 65 that has a square wave pulse each time that the reference material is aligned with the optical fibers 31, 32 is fed to the gate 71 for closing the gate 71 only when the reference material is aligned between the optical fibers 31, 32 so that only the reference attenuation signal is passed to the amplifiers 72, 73 and the peak detector 74. The differential amplifier 75 will compare the reference attenuation signal from the peak detector 74 with a voltage reference from the component 66 and produce a differential output that is sent to the lamp control 76. Although it is advantageous to provide only one voltage reference 66 for both the sample circuit and reference circuit, it is contemplated that separate voltage references may be used if convenient. With the oil monitor in perfect operating condition, the reference attenuation signal fed to the differential amplifier 75 will be identical to the voltage reference fed from the reference 66 so that there will be no output from the differential amplifier 75 and the lamp control will not change the current supplied by the lamp power supply 77 to the light source 27; thus, the intensity of the light source 27 will not change during ideal operating conditions. If the lamp power supply should fluctuate or change producing a corresponding change in the lamp intensity or if discoloration should appear on the faces of the optical fibers, windows, filters or reference material ends, or the characteristics of the electrical components should change, etc., there would be a change in the reference attenuation signal fed through the attenuation reference circuit, which would produce a corresponding error signal from the differentil amplifier 75 that would provide a feedback to the lamp control 76 for regulating the output of the lamp's power supply 77 and thus regulating the intensity of the light source 27 for correction purposes. Thus, the light source, electrical components and mechanical components will not affect the readings of the oil monitor in that the system is self-regulating. If there is no reference attenuation signal reaching the differential amplifier 75, the malfunction indicator 78 will be energized to show that there is a breakdown somewhere in the system of the oil monitor.

When rotor 17 is provided with vanes and is mounted for free rotation, the speed with which it rotates will correspond to the flow of the oil through the oil monitor sensor of FIG. 1. Thus, the frequency of the light pulses reaching the photo-transistor 39 will be correlated to the speed and similarly the control signal produced by the photo-transistor 39 will have a frequency correlated to the fluid flow. A frequency responsive flow gauge 79 is connected in circuit with the control signal outputs 65 to provide a convenient reading of oil flow.

The scattering signal produced by the photo-transistor 44 will be composed of alternating sample of reference pulses, which will be fed by line 80 to the input of signal amplifier and D.C. eliminator 81, which functions in a manner identical to the signal amplifier and D.C. eliminator 51. The output of amplifier 81 is split and fed by line 82 to the parallel scattering sample circuit 83 and the scattering reference circuit 84. The scattering sample circuit 83 comprises in series a field effect transistor gate 85 that is shown in the open position because the sample is not aligned with the optical fibers 31 and 32 in the other figures of the drawing, amplifier 86, calibration component 87, amplifier 88, peak detector 89, and scattering output indicator or gauge 90. The output control signal of line 64 that has a pulse each time that the sample is aligned with the optical fibers 31 and 32 is fed to the gate 85 for closing the gate and thus passing only the sample component of the scattering signal in line 82. The sample component of the scattering signal is thereafter fed through the components 86, 87, 88, 89 and 90 for their respective functions to produce an indication of the particle contamination. The scattering reference circuit 84 comprises in series a field effect transistor gate 91, which is shown in its closed position because in all of the other figures the reference is shown aligned with the optical fibers 31 and 32, an amplified 92, an amplifier 93, a peak detector 94, an error differential amplifier 95, and a servomechanism 96. The scattering reference signal that has been passed through the components 92, 93, 94 is fed to the error differential amplifier 95 along with a reference signal from scattering reference 97 to produce a scattering error signal that is applied to the servomechanism 96 for operation of the calibration component 87 to adjust the gain on the amplifier 88. The servomechanism 96 may be also replaced with corresponding electrical feedback circuit components that serve the same function. Thus, with a weakening of the scattering signal volume, the volume may be correspondingly increased by the feedback of scattering reference circuit 84 so that the signal that ultimately reaches gauge 90 will be sufficiently strong to assure proper operation of the gauge. Thus, the scattering circuit is self-regulating with respect to volume only, that is, the feedback function of scattering reference 84 will not affect the particle detecting function of peak detector 89 and the gauge function in summing the peak signals corresponding to contamination by particles but will maintain sensitivity of the instrument at some desired preset level.

The above circuit may be modified in many ways without departing for the spirit of the present invention; for example, the malfunction light may be actuated by an excessive error signal coming from the error differential amplifier 75, the photo-transistors may be replaced by photo-resistive elements, etc.

OPERATION

Although the operation of the oil monitor has been described above in connection with the detailed description of the various components, it will be summarized below.

The oil monitor sensor of FIG. 1 may be placed in the lubrication oil sump for an aircraft engine. The rotor 17 may be freely rotatable as shown so that the engine oil pump will circulate oil through the sensor from aperture 4 to aperture 5, or from aperture 5 to aperture 4 so that the blades 24 will act as turbine blades to rotate the rotor 17. As the rotor 17 rotates, the through passage 22 containing therein the reference material 24 will move into alignment with the optical fibers 31, 32 alternately with the diametrically opposed through passage 22 which has the oil circulating therethrough. Besides the pumping action of the engine oil pump, the oil will move through the sample passage 22 by the centrifugal action of the radial outlet 25, which would preferably be located at the exit end for this purpose depending upon the direction of fluid flow. If the oil is static, where the sensor is placed, a motor may be provided to rotate the rotor 17 and provide pumping action by the blades 24 and the radial outlet 25 for moving the oil through the sensor. Also, the sensor could be placed in an oil line with a motor attached to the stub shaft 18 of the rotor 17 so that the sensor itself would act as the engine oil pump.

With the oil sample in its passage 22 and the reference material 23 alternately passing in alignment with the light source optical fiber 31 as mentioned above, the attenuation optical fiber 32 will pick up light pulses that will correspondingly alternate between light pulses from the oil sample and the reference material 23. Similarly, the optical fiber 42 will pick up corresponding scattering light pulses from the oil sample wherein contamination particles will cause the light to scatter in a plane perpendicular to the axis of the passage 22 for travel through additional radial passsage 46 and from the sample material 23 with known light scattering characteristics, which will scatter the light in a plane perpendicular to its passage 22 for travel through the radial additional passage 41. The photo-transistor 34 which receives the attenuation light pulses through optical fiber 32 will produce electrical signals correlated to the degree of attenuation of light caused respectively by the oil sample and the reference material 23; the attenuation produced by the oil sample will increase with chemical breakdown of the lubricating oil. The photo-transistor 44 will produce electrical signals that will pulse in correlation with the exciting scattering light pulses received by optical fiber 42 for providing a scattering reference signal and a scattering or oil contamination signal. Also during rotation of the rotor 17, the reflective surface 36 will cause light from the optical fiber 31 to be reflected through the optical fiber 37 for exciting the photo-transistor 39; thus, the photo-transistor 39 will produce an electrical control signal pulse each time the reflective surface 36 passes the optical fiber 31, that is, each time the reference material 23 passes the optical fiber 31.

With particular reference to FIG. 9, it is seen that the attenuation sample and reference signals from the photo-transistor 34 will pass through the common line 50 to each of the attenuation sample circuits 53 and the attenuation reference circuit 54. The control signal produced by photo-transistor 39, which will have a pulse each time that there is a reference attenuation pulse from the photo-transistor 34, will be amplified and clipped at 63 to the indicated wave form in output line 65, which is connected to the field effect transistor gate 71; thus, the gate 71 will be closed each time that there is a reference pulse from the photo-transistor 39, that is correspondingly each time there is a reference attenuation pulse from the photo-transistor 34. Therefore, the gate 71 will only pass the attenuation reference signal as indicated by the wave form adjacent amplifier 72. This attenuation reference signal will be compared with the reference voltage from 66 by the differential amplifier 75 to produce an output that will excite the malfunction indicator light 78 if there is an extreme breakdown in the system. The differential output of the differential amplifier 75 will operate the lamp control 76 to adjust the lamp power supply 77 for regulating the intensity of the light source 27 so as to maintain a relatively constant output of the attenuation reference signal, which has the result of compensating for fluctuations or changes in the lamp power supply 77, changes in the efficiency of the light source 27, changes in the optical properties of the optical fibers 31, 32, changes due to discoloration, etc., of the windows in the rotor 17, etc.

The control signal from line 62 will also be amplified, clipped and phase inverted to produce the wave form shown in output line 64, which is thereafter fed to the field effect transistor gate 55 for closing the gate 180° out of phase with the closing of the gate 71, which will have the result that gate 55 will pass only the sample attenuation signal as shown by the wave form adjacent the amplifier 56. The sample attenuation signal will be compared with the reference voltage from 66 by the differential amplifier 60, to produce a differential output that will operate gauge 61 for indicating the oil attenuation or chemical breakdown. Test switches 67 and 70 may be operated jointly to pass the control output signal from line 65 to gate 55, which will have the result that only the reference attenuation signal will be passed through the amplifier 56 for calibration of gauge 61 by means of the calibration circuit 57 to give a zero reading of the gauge that would correspond to new clean oil. During such calibration, the zero signal output from amplifier 58 may be used to adjust the full scale position of the gauge 61 that would correspond to oil that would pass no light, or have full attenuation.

The reference and sample scattering signals produced by the photo-transistor 44 will be fed through the common line 80 to both the scattering sample circuit 83 and the scattering reference circuit 84. With operation similar to that of gate 55, the gate 85 will close, in response to the output control signal from line 64, to pass only the sample scattering signal as shown by the wave adjacent the amplifier 86, which will pass through the amplifier gain control calibration component 87 to be peak detected at 89 to produce a signal fed to the gauge 90 that will correspond to the particle count for producing an indication on the gauge 90 of the particle contamination within the oil. For the scattering reference circuit 84, the gate 91 will operate similar to the gate 71 previously described by responding to the control output signal in line 65 for passing only the scattering reference signal as shown by the wave form adjacent the amplifier 92. This scattering reference signal will be amplified at 92, 93, peak detected at 94, and compared by the error differential amplifier 95 with a reference signal from 97. The differential output of the error amplifier 95 will operate the servo-mechanism 96 to adjust the gain in the sample scattering circuit 83 at the calibration component 87 to produce a signal that will be strong enough to be peak detected at 89 for summation of the particle signals to properly operate the gauge 90 even when oil attenuation reduces the amount of scattered light reaching the photo-transistor 44, to thus compensate for attenuation that would otherwise complicate the particle contamination monitoring.

The scattering sample circuit 83 may be calibrated in the previously described manner of the attenuation sample circuit by depressing switch 70 to pass the reference signal.

Since one pulse will be produced in the control line 62 for each revolution of the rotor 17, a frequency responsive flow guage 79 is connected in circuit to receive the control output signal from line 65 and indicate flow rate, which flow rate is proportional to the speed of rotation of rotor 17.

With the modification of FIGS. 6–8, the circuitry for two opposed through passages 22' containing therein the reference material 23' and the filter window 47, respectively, will be identical in structure and operation with that shown in FIG. 9. The circuitry for the other opposed through passages 22' containing therein a different reference material and filter window 48 will include all of the components set forth in FIG. 9, except for the feedback attenuation reference circuit 54, because the same light source 27, optical fibers 31, 32 and photo-transistors 34, 44 would be involved in monitoring all of the passages 22'. Also, another flow gauge 79 would not be necessary. In addition to the amplifier, clipper and phase inverter 63, there would be a 90° phase shifter for each of the output lines 64, 65 to correspond with the 90° offsetting of adjacent through passages 22' in the rotor 17'.

Since the basic circuitry for the modification of FIGS. 6–8 is shown in FIG. 9 and the above changes are minor, it is thought that no further explanation is necessary for the proper understanding of the modification by a person having ordinary skill in the art.

Figure 2:
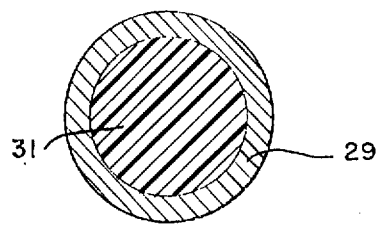
FIG. 2 is a cross sectional view through an optical fiber element controlling the passage of light taken along line II—II in FIG. 1.

Also, it is contemplated that the reference material passage and sample passage according to the embodiment of FIGS. 1–5 could be duplicated in opposed passages 90° offset from those shown in FIG. 2, for example, to double the frequency of the signals produced by photo-transistors 34, 44. Correspondingly, an additional reflective surface 36 will be provided adjacent the additional through passage 22 that would hold the same sample material 23. The circuitry of FIG. 9 would remain identical to what is now shown. Of course, the various guages and controls would necessarily have to be recalibrated for the double frequency.

As a further modification, the rotor attenuation reference would be shortened so that the portion of the reference light path between the end of the lamp fiber optics, to just short of the scattering photo-transistor, is filled with oil. Therefore, if the attenuation of this portion of the light path should increase, there will be a corresponding increase in lamp intensity, to prevent a reduction in the scattering signal.

Several embodiments, modifications and variations have been shown and described to illustrate that the basic principles and inventive features of the preferred embodiment are contemplated to be used in further and widely different applications according to the spirit and scope of the invention.

I claim:

1. Apparatus for testing a sample of fluid material to determine at least one characteristic correlated to the effect the material has on light comprising a sealed chamber for containing therein a fluid sample to be tested and having inlet and outlet openings thereto for the fluid sample to be tested; a light source mounted exteriorly of said chamber, means responsive to light for producing a signal mounted exteriorly of said chamber; first optical fiber means extending from within said chamber to said light source; second optical fiber means extending from within said chamber to said light responsive means, a rotor mounted for rotation about an axis within said chamber; said rotor having at least two through passages, each extending between the chamber ends of said optical fiber means in spaced-apart positions of said rotor; a reference material in one or more of said passages, and means in other of said passages for holding a sample material; second light responsive means; third optical fiber means extending from within said chamber to said second light responsive means and having an off-axis orientation with respect to said first and second optical passages in said rotor providing respective light paths for each of said through passages with said third optical fiber means.

2. Apparatus according to claim 1 further including a plurality of fluid reaction vanes mounted on the periphery of said rotor for reacting on a fluid sample contained within said chamber while said rotor is rotating.

3. Apparatus according to claim 1 further including means formed on said rotor for intercepting and diverting light from said light source along a third light path and third light responsive means disposed in said third light path for deriving synchronizing control signals used in the processing of the output signal from said first and second light responsive means.

4. Apparatus according to claim 1 further including means disposed in said means for holding a sample for matching discoloration effects of said reference material to samples being held.

5. Apparatus according to claim 1 further including means formed on said rotor for intercepting and diverting light from said light source along a third light path and third light responsive means disposed in said third light path for deriving synchronizing control signals used in the processing of the output signal from said first and second light responsive means further including means disposed in said means for holding a sample for matching discoloration effects of said reference material to samples being held.

6. Apparatus according to claim 5 further including a plurality of fluid reaction vanes mounted on the periphery of said rotor for reacting on a fluid sample contained within said chamber while said rotor is rotating.

7. Apparatus for testing a sample of fluid material to determine at least one characteristic correlated to the effect the material has on radiant energy comprising means for holding a sample fluid material; separate means for holding a reference material having known radiant energy affecting characteristics; a single radiant energy source; means for passing a single radiant energy beam from said source alternately through each of said means for holding to alternately pass the radiant energy beam through sample and reference material; single attenuated radiant energy responsive means for intercepting the attenuated radiant energy after it has passed through said means for holding a sample material and after it has passed through said means for holding a reference material to produce an attenuation electrical output comprised of correspondingly alternating sample and reference attenuation electrical signals in response to the radiant energy intercepted by said attenuated radiant energy responsive means including a single radiant energy to electrical energy transducer receiving the attenuated radiant energy from only one direction common to sample and reference radiant energy; and single scattered radiant energy responsive means mounted with respect to said holding means and said means for passing radiant energy so that it receives the radiant energy scattered by said materials to produce a single scattered electrical output correspondingly alternating between sample and reference scattered electrical signals, and including a single radiant energy to electrical energy transducer receiving the scattered radiant energy from only one direction common to sample and reference radiant energy.

8. The apparatus of claim 7 wherein the radiant energy is light.

9. The apparatus of claim 7 further including means utilizing at least one of the reference electrical signals to regulate the signal processing of the sample electrical signals.

10. The apparatus of claim 7, including first separating means receiving said scattered electrical output and producing a first separated output of only said sample scattered signal and a second separated output of only said reference scattered signal; means utilizing said reference scattered signals for regulating the signal processing of the sample scattered signal; second separating means receiving said attenuation electrical output and producing a first separated output of only said sample attenuation signal and a second separated output of only said reference attenuation signal; and means utilizing the reference attenuation signal for regulating the signal processing of the sample attenuation signal.

11. Apparatus according to claim 7 further including means for intercepting radiant energy from said source as it is alternately passed through sample and reference material and for diverting the intercepted radiant energy along a predetermined path, and a single synchronizing radiant energy to electrical energy transducer disposed in the predetermined path for deriving synchronizing electrical signals useful in the processing of the sample and reference attenuation and scattered electrical signals.

12. Apparatus according to claim 7 further including means disposed in said means for holding a sample fluid material for matching discoloration effects of said reference material to the sample fluid materials being held.

13. Apparatus according to claim 7 further including means for intercepting radiant energy from said source as it is alternately passed through sample and reference material and for diverting the intercepted radiant energy along a predetermined path, and a single synchronizing radiant energy to electrical energy transducer disposed in the predetermined path for deriving synchronizing electrical signals useful in the processing of the sample and reference attenuation and scattered electrical signals and further including means disposed in said means for holding a sample fluid material for matching discoloration effects of said reference material to the sample fluid materials being held.

14. Apparatus according to claim 13 further including means coupled to said single synchronizing radiant energy to electrical transducer for producing two separate alternate gate control signals of the same frequency as the reference and sample attenuation and scattered signals, first and second gate means connected in parallel circuit relationship and supplied with said reference and sample attenuation and scattered signals, said first gate means being responsive to said first gate control signal for passing only the reference attenuation and scattered signals and said second gate means being responsive to said second gate control signal for passing only the sample attenuation and scattered signals; means for producing a standard signal; first differential amplifier means receiving said standard signal and the signal passed through said second gate means as its input and producing a first differential output signal; indicator means responsive to said first differential output signal; second differential amplifier means receiving said standard signal and the signal passing through said first gate means as its input and producing a differential output error control signal; and means for feeding back said output error control signal for regulating the signal processing of said sample attenuation and scattered signals.

15. The apparatus according to claim 14, including means for selectively applying only said first gate control signal to both of said gate means; and calibration means for separately increasing or decreasing the signal passing through said one of said gate means before reaching said first differential amplifier for reducing to zero the output of said first differential amplifier when said first gate control signal is selectively fed to said second gate means for zero calibration.

16. The apparatus of claim 7, including sample circuit means receiving at least one of said separated signals for indicating at least one sample characteristic; reference circuit means receiving at least one of said separated reference signals for comparing the one reference signal with a standard signal and producing an output error signal proportional to the difference between the one reference signal and the standard signal, and means utilizing the output error signal to regulate the signal processing of the sample signal.

17. The apparatus of claim 16 wherein the radiant energy is light.

18. Apparatus according to claim 17 further including means for intercepting radiant energy from said source as it is alternately passed through sample and reference material and for diverting the intercepted radiant energy along a predetermined path, and a single synchronizing radiant energy to electrical energy transducer disposed in the predetermined path for deriving synchronizing electrical signals useful in the processing of the sample and reference attenuation and scattered electrical signals.

19. Apparatus according to claim 17 further including means disposed in said means for holding a sample fluid material for matching discoloration effects of said reference material to the sample fluid materials being held.

20. Apparatus according to claim 17 further including means for intercepting radiant energy from said source as it is alternately passed through sample and reference material and for diverting the intercepted radiant energy along a predetermined path, and a single synchronizing radiant energy to electrical energy transducer disposed in the predetermined path for deriving synchronizing electrical signals useful in the processing of the sample and reference attenuation and scattered electrical signals and further including means disposed in said means for holding a sample fluid material for matching discoloration effects of said reference material to the sample fluid materials being held.

21. Apparatus according to claim 20 further including means coupled to said single synchronizing radiant energy to electrical energy transducer for producing two separate alternate gate control signals of the same frequency as the reference and sample attenuation and scattered signals; first and second gate means connected in parallel circuit relationship and supplied with said reference and sample attenuation and scattered signals, said first gate means being responsive to said first gate control signal for passing only the reference attenuation and scattered signals and said second gate means being responsive to said gate control signal for passing only the sample attenuation and scattered signals; and means for selectively applying only said first gate control signal to both of said gate means.

22. Apparatus for testing a sample of material to determine at least one characteristic correlated to the effect the material has on light, comprising means for holding a sample material; separate means for holding a reference material having known light affecting characteristics; means for passing light separately through each of said means for holding to pass through held material and a reference material and including only a single light source; a single light responsive means for intercepting the light after it has passed through said holding means for holding a sample material and after it has passed through said means for holding a reference material to produce sample and reference signals in response to the light intercepted; all of said holding means being rigidly interconnected equidistant from an axis as a holding unit, and said means for passing light and said light responsive means being rigidly interconnected as a light unit; said holding unit being rotatably mounted about the axis with respect to said light unit to selectively align only one of said means for holding with the light at one time; a motor having an independent power source and being drivingly connected for rotating said holding unit about the axis; and a plurality of pump blades mounted on said holding unit for rotation therewith to pump fluid through said means for holding a sample material during rotation of said holding unit.

23. Apparatus for testing a sample of material to determine at least one characteristic correlated to the effect the material has on light comprising means for holding a sample material; separate means for holding a reference material having known light affecting characteristics; means for passing light separately through each of said means for holding to pass through held material and a reference material and including only a single light source; a single light responsive means for intercepting the light after it has passed through said means for holding a sample material and after it has passed through said means for holding a reference material to produce sample and reference signals in response to the light intercepted; said holding means being rigidly interconnected equidistant from an axis as a holding unit, and said means for passing light and said light responsive means being rigidly interconnected as a light unit; said holding unit being rotatable about the axis with respect to said light unit to selectively align only one of said means for holding with said light at one time; and means for passing a stream of fluid sample through said means for holding a sample material and past said holding unit; and a plurality of turbine vane means mounted on said holding unit for rotation therewith within the fluid sample stream for driving the holding unit about the axis.

24. The apparatus according to claim 23 including means for measuring the holding unit speed of rotation produced by said turbine vanes and indicating the correlated fluid flow.

25. Apparatus for testing a sample of material to determine at least one characteristic correlated to the effect the material has on light comprising a sealed chamber containing therein a fluid sample to be tested; a light source mounted exteriorly of said chamber; means responsive to light for producing a signal mounted exteriorly of said sealed chamber, first optical fiber means extending from said light source into said chamber; second optical fiber means extending from within said chamber to said light responsive means; a rotor mounted for rotation about an axis within said chamber; said rotor having at least two through passages, each extending between the chamber ends of said optical fiber means in spaced-apart positions of said rotor; a reference material in one of said passages, and means in other of said passages for holding a sample material; said chamber comprising a first tubluar wall having said rotor mounted therein for rotation about an axis parallel to the axis of symmetry of said tubular wall, and having said optical fibers extending therethrough, and being opened at opposed ends for respectively receiving and discharging fluid sample material.

26. The apparatus according to claim 25 including a second wall radially spaced outwardly from said first tubular wall and sealing means between said second wall and said first tubular wall forming together a chamber containing therein said light source and means responsive to light.

27. The apparatus according to claim 26 wherein said second wall is tubular and said sealing means includes a radially extending flange integral with one of said tubular walls and engaging the entire periphery of the other of said tubular walls at one of their ends, and a mounting member sealingly engaging the entire periphery of the other ends of said tubular walls; said mounting member having means for mounting it to a support surface and providing the sole, cantilever support for said tubular walls.

28. Apparatus for optically monitoring the condition of a moving stream of fluid, comprising means for holding at least a moving portion of the fluid stream; means for holding an at least partially light transmitting reference material; light source means; light responsive transducer means for converting received light into correlated electrical signal output; light path means alternately forming a first light path between said light source means, said reference material holding means and said light responsive transducer means, and a second light path between said light source means, said moving fluid portion holding means and said light responsive transducer means; and said light path means including a light path portion for each of said paths mounted for free rotation about an axis generally aligned with the direction of flow for the moving fluid stream, and turbine means for rotatably driving said light path portion about said axis, including a plurality of turbine blades in the fluid stream mounted on said light path portion about said axis.

* * * * *